United States Patent
Postmes

(10) Patent No.: US 11,160,272 B2
(45) Date of Patent: Nov. 2, 2021

(54) METHODS FOR PRESERVING TISSUE WITH MEDICAL GRADE HONEY

(71) Applicant: TRITICUM EXPLOITATIE B.V., Maastricht (NL)

(72) Inventor: Josephus Petrus Lidwinus Postmes, Maastricht (NL)

(73) Assignee: TRITICUM EXPLOITATIE B.V., Maastricht (NL)

( * ) Notice: Subject to any disclaimer, the term of this patent is extended or adjusted under 35 U.S.C. 154(b) by 0 days.

(21) Appl. No.: 16/764,575

(22) PCT Filed: Nov. 15, 2018

(86) PCT No.: PCT/NL2018/050768
§ 371 (c)(1),
(2) Date: May 15, 2020

(87) PCT Pub. No.: WO2019/098833
PCT Pub. Date: May 23, 2019

(65) Prior Publication Data
US 2020/0396986 A1    Dec. 24, 2020

(30) Foreign Application Priority Data
Nov. 15, 2017  (NL) ..................................... 2019918

(51) Int. Cl.
*A61K 35/644*    (2015.01)
*A01N 1/02*      (2006.01)

(52) U.S. Cl.
CPC .......... *A01N 1/0226* (2013.01); *A61K 35/644* (2013.01)

(58) Field of Classification Search
None
See application file for complete search history.

(56) References Cited

U.S. PATENT DOCUMENTS

| 2004/0131693 A1* | 7/2004 | Postmes ............. A61K 2300/00 424/539 |
| 2008/0292560 A1* | 11/2008 | Tamarkin ............... A61K 8/046 424/45 |
| 2015/0030688 A1 | 1/2015 | Sell et al. |

FOREIGN PATENT DOCUMENTS

| CN | 1044575 A | 8/1990 |
| DE | 2024341 | 12/1971 |
| GB | 1253340 A | 11/1971 |
| RU | 2123259 C1 | 12/1998 |
| SU | 1082362 A1 | 3/1984 |
| SU | 1367931 A1 | 1/1988 |
| WO | 2019/098833 A1 | 5/2019 |

OTHER PUBLICATIONS

Morris, C. The Use of Honey in Wound Care and the Mesitran Product Range. Wounds UK 4(3)84-87, Sep. 2008. (Year: 2008).*
Nolan, V. et al. Dissecting the Antimicrobial Composition of Honey. Antibiotics 8(4)1-16, Dec. 2019. (Year: 2019).*
International Search Report of related PCT/NL2018/050768, dated Apr. 16, 2019, 11 pages.
Subrahmanyam, "Storage of skin grafts in honey." Lancet. Jan. 2, 1993;341(8836):63-4.
Pimenta J. et al., "Medical Grade Honey in Ovarian Cortex Preservation: An in vitro Animal Model Approach for Studying Angiogenesis (Abstiact 22)", Nov. 16, 2017, 5th World Congress of the International Society for Fertility. Retrieved from the Internet: URL:http://cme-utilities.com/mailshotcme/Material%20for%20Websites/ISFP/abstracts/22.pdf, 2 pages.
Chen L, "Experimental Studies of Hetrotransplantation of the Cornea", Folia Ophthalmologica Japonica,vol. 38, No. 11, Jan. 1987, p. 1652-1659.
Anonymous, "List of Posters Presentations", Nov. 12, 2017, 5th World Congress of the International Society for Fertility Preservation Retrieved from the Internet: URL:https://www.isfp2017.cme-congresses.com/posters, 3 pages.

* cited by examiner

*Primary Examiner* — Ralph J Gitomer
(74) *Attorney, Agent, or Firm* — Casimir Jones, S.C.; Tanya A. Arenson

(57) ABSTRACT

The present invention relates to the use of a medical grade honey based ingredient for the preparation of a composition for preserving human and/or animal tissue. In addition, the present invention relates to the use of a medical grade honey based ingredient for the preparation of a composition for preserving human and/or animal tissue through the promotion of angiogenesis.

6 Claims, No Drawings

METHODS FOR PRESERVING TISSUE WITH MEDICAL GRADE HONEY

The present invention relates to the use of a medical grade honey (MGH) based ingredient for the preparation of a composition for preserving human and/or animal tissue. In addition, the present invention relates to the use of a medical grade honey (MGH) based ingredient for the preparation of a composition for preserving human and/or animal tissue through the promotion of angiogenesis.

GB 1,253,340 relates to the preservation of organic material and is concerned with a medium for preserving human tissues and organs, such as bones, articulary cartilage, tendons and skin, whilst maintaining same in a condition suitable for use in transplant operations. The medium for the conservation of those tissues and organs, comprising a mixture of hydrated gelatine, 15-25 parts, glycerine 3-7 parts, polyflower honey, honey derived from a plurality of different kinds of flowers rather than from one kind of flower only, quantum satis ad 100 parts, decamethylene bis 4 amino quinaldine chloride or dimethylalkyl benzyl ammonium chloride, 1/5009-1/iCOOf) parts by weight of the total medium. This GB document refers to transplant operations and does not specifically state fertility preservation and encompasses temperatures down to 4 degrees Celsius for preservation, whereas the temperatures pertaining to reproductive tissue preservation and cryopreservation reach sub-zero values.

In the article of R. Al-Maaini and P. Bryant, "Honey as an Alternative to Formalin in the Demonstration of Connective Tissue Components", The Journal of Histotechnology 2008, volume 31, no. 2, pages 67-72, the use of 10% honey as an alternative to formalin in the histological demonstration of connective tissues without the need for amendments to existing laboratory protocols is mentioned. The function of fixation in cellular pathology is to preserve tissues in a life-like condition by preventing both autolysis and putrefaction. Formalin is the most widely used fixative because of its ease of use, low cost, and speed of fixation. The type of honey used in this work was obtained from the Al-Qabel desert in the Sultanate of Oman. The technical difficulties in this article include autolysis, putrefaction and safety concerns, whereas fertility preservation and touch specifically upon ischemia-reperfusion injury and/or apoptosis. The article further suggests the use of honey as a substitute for histology lab use and compatibility with staining—appears to be more of a histological fixative.

RU 95101881 relates to a method for cartilage preservation in physiological saline with the addition of an antibiotic wherein the cartilage taken during the operation is treated with physiological saline with an antibiotic for 1 minute, then placed in a glass container with buckwheat honey and stored at 4-5° C. The present invention does not encompass cartilage nor tendon preservation. The temperature range of this RU document is down to 4-5 degrees Celsius, unlike the temperatures implicated in cryopreservation of reproductive material.

The article of K. Rossiter et al. "Honey promotes angiogeneic activity in the rat aortic ring assay", Journal of Wound Care, 2010, volume 19, no. 10, pages 440-446, relates to the investigation of possible effects of honey on angiogenesis in a wound dressing context, using in vitro analogues of angiogenesis and an endothelial proliferation assay. This article highlights a study that is not performed within the fertility context, since the tissue is aortic and the authors do not mention extrapolation to the reproductive setting.

US 2015/030688 relates to tissue engineered scaffold comprising a fiber support and honey, further comprising at least one biomolecule, wherein the at least one biomolecule is selected from the group consisting of a growth factor, a cytokine, a bioactive lipid, an immunoglobulin, and combinations thereof, wherein the at least one biomolecule is a preparation rich in growth factors, wherein the fiber support is selected from the group consisting of an electrospun fiber support, an electroblown fiber support, an extruded fiber support, a fiber sheet, and a film support. This document is not pertaining to tissue preservation but essentially replacement—hence it is distanced from fertility preservation.

WO 2007/137369 relates to a method of treating an ophthalmic, respiratory or ear condition in a subject, the method comprising administering to the subject a therapeutically effective amount of a medicinal composition comprising a honey having non-peroxide antibacterial activity, wherein the composition comprises about 19% to about 80% water by weight.

In vitro and in vivo studies have highlighted a broad range of activities provided by honey in burn treatment. These include anti-infectious, anti-inflammatory, antiexudative, antioxidant, wound healing, wound debriding and nutritional properties. Honey is a viscous concentrated solution of sugars produced by bees (Apis mellifera) that collect and process the blossom nectar (flowers or floral honey) or sweet juices on certain plant species (honeydew or forest honey). Honey is one of the most complex and valuable natural biological products used since ancient times, both in nutrition and medicine (through internal and external means). None of the above discussed publications are concerned with ovarian tissue preservation and later transplantation. The ovarian tissue preservation and later transplantation represents one of the most promising techniques in the preservation of fertility in particular in the case of cancer patients who are at risk of total or partial loss of ovarian function due to chemotherapy or radiation treatments. To date three hundred nine autologous ovarian tissue transplantations were performed with cryopreserved tissue, resulting in the birth of 84 children and 8 ongoing pregnancies. The cumulative clinical and live+ongoing rates were 57.5% and 37.7%, respectively, and the endocrine restoration rate was 63.9%, suggesting that ovarian tissue cryopreservation should be considered as a viable option for fertility preservation.

However, there are also many drawbacks such as ischemia in the early stage after ovarian graft that causes massive follicle loss by apoptosis. In fact, the formation of an individual capillary network around each follicle is required for follicles to grow beyond the secondary stage, which contains multiple layers of granulosa cells and theca cells. As the follicle continues to develop, endothelial cells are recruited to the theca cell layer from the blood vessels in the adjacent ovarian stroma, supporting the notion that angiogenesis plays a crucial role in follicular growth and in selection of the ovulatory follicle.

The object of the present invention is to overcome the technical difficulties in preserving human/animal tissue.

The present invention thus relates to the use of a medical grade honey based ingredient for the preparation of a composition for preserving human and/or animal tissue. The present invention thus relates to a composition comprising a medical grade honey based ingredient for use in preserving human and/or animal tissue.

The present invention also relates to the use of a medical grade honey based ingredient for the preparation of a composition for preserving human and/or animal tissue through the promotion of angiogenesis. The present invention thus relates to a composition comprising a medical grade honey based ingredient for use in preserving human and/or animal tissue through the promotion of angiogenesis.

The present invention here falls into the technical area of tissue preservation, in this case within the specific context of fertility preservation, as it pertains to ovarian tissue. The present application reflects further on other types of tissue preservation, human and/or animal ovarian follicles and/or sperm cell viability through use of a medical grade honey based ingredient.

In an embodiment of the present invention the human and/or animal tissue is human and/or animal ovarian tissue. The present invention thus relates to the use of a medical grade honey based ingredient for the preparation of a composition for preserving human and/or animal ovarian tissue. The present invention thus relates to a composition comprising a medical grade honey based ingredient for use in preserving human and/or animal ovarian tissue.

In an embodiment of the present invention the human and/or animal tissue is human and/or animal ovarian follicles. The present invention thus relates to the use of a medical grade honey based ingredient for the preparation of a composition for preserving human and/or animal ovarian follicles. The present invention thus relates to a composition comprising a medical grade honey based ingredient for use in preserving human and/or animal ovarian follicles.

In an embodiment of the present invention the human and/or animal tissue is sperm cell viability. The present invention thus relates to the use of a medical grade honey based ingredient for the preparation of a composition for preserving human and/or animal sperm cell viability. The present invention thus relates to a composition comprising a medical grade honey based ingredient for use in preserving human and/or animal sperm cell viability.

Methods to aid in ovarian tissue preservation involve the enhancement of angiogenesis through pro-angiogenic agents in an attempt to support follicular growth and viability (Akiyama et al, 2014; Robinson et al, 2009). The classic promoter of angiogenesis is the vascular endothelial growth factor (VEGF), hence justifying the choice for comparison against the honey-based preparation.

A current commonly used reagent for this purpose, Vascular Endothelial Growth Factor (VEGF) presents disadvantages such as elevated cost, reduced half-life and potential for vascular leakage in the early stage after ovarian graft that causes massive follicle loss by apoptosis and ischemia. The present inventors found that the honey based preparation demonstrated tendency to reduce cytotoxicity, whilst VEGF had an increasing tendency. VEGF has also become a promising factor in vascular targeted therapy for patients with resistant and recurrent ovarian cancer, which would prevent its use for the purpose at hand.

Medical Grade Honey (MGH) (i.e. clean from pesticides. herbicides, antibiotics. heavy metals, dormant endospores etc.—see Postmes. 1993, *Lancet.* 1993 Mar. 20; 341(8847): 756-7) further preferably comprises Vitamin C, Vitamin E. Lanolin and Polyethylene Glycol. Medical Grade Honey has been sterilised through irradiation, especially gamma irradiation, and is free from contaminants. An embodiment of MGH is Manuka honey, i.e. honey from the nectar of the Manuka tree, also known as active Manuka honey if it has a UMF (Unique Manuka Factor) rating of over 10. The key unique signature markers of Manuka honey—Leptosperin, Methyglyoxal and DHA—must all be present in the honey, not just one in isolation, wherein the UMF grading number is based on the combined levels of these key signature markers, wherein UMF is the only testing and grading system that is based on the combined levels of the key Manuka signature markers. From EP 1 239 742 am medical grade honey is known. The composition of that medical grade honey is here referred to.

The present composition preferably comprises eco-honey (CAS 8028-66-8) in an amount of 20-60% w/w, preferably 30-50% w/w. The present composition further preferably comprises hypo allergenic lanolin (CAS 8006-54-0) in an amount of 5-20% w/w. The present composition further preferably comprises one or more components chosen from the group of PEG (CAS 57-55-6), PEG 4000 (CAS 25322-68-3), ascorbic acid (CAS 50-81-7), Vitamin A, Vitamin D, Vitamin E, and Omega 3. These ingredients may play a key role in providing solutions to the above mentioned issues: one possible solution to reduce ischemic damage is enhancing angiogenesis of the ovarian cortex tissue and the present honey based preparation does that. The afore mentioned percentages are based on the total weight of the final composition. All the components in the composition account for a total of 100% w/w. In other words, all individual percentages of the components will attribute to a total of 100% w/w.

Current methods show a relative high cytotoxicity detrimental to new tissue formation. Additionally success rates are variable with VEGF and furthermore there is the problem of reducing oxidative stress during the processes involved. The present honey based preparation has the advantage that the cytotoxicity is significantly lower thereby providing for more tissue generation and as such speed up the process of angiogenesis.

One possible solution to reduce ischemic damage is enhancing angiogenesis of the ovarian cortex tissue. In this application the present inventors used the bovine animal model to study the in vitro effect of a medical grade honey (L-Mesitran, Soft and Ointment) and the Vascular Endothelial Growth Factor (VEGF; a classical stimulator of angiogenesis) in the ovary cortex vascular content. Humans and cattle share numerous characteristics regarding ovarian physiology and follicular development, making the cow the best model for this purpose.

Methods

Four mature crossbred beef cows (12 months of age) were used for this study. After collection in a local abattoir, the bovine ovarian cortex tissue samples (dissected from medulla and further cut into ultra-thin strips) were cultured in vitro [TCM-199 medium with 10% cow serum] and distributed in four groups, including (1) blank control group, (2) VEGF (50 ng.mL-1) group, (3) L-Mesitran Soft (0.2%) group, and (4) L-Mesitran Ointment (0.2%) group. The 0.2% v/v concentration (L-Mesitran) was chosen according to the highest reported pro-angiogenic effect for this medical grade honey in an in vitro tissue culture. The ovarian cortex endothelial immunolocalization was quantified using Factor VIII [9] R Ag. Rabbit Polyclonal Antibody (ref 760-2642; BenchMark ULTRA IHC/ISH Module staining protocol; Ventana Medical Systems, Inc.; Roche, USA) at concentrations of 2.26□g/ml, and Fiji software [10] for the digital analysis, after 0 h, 4 h, 24 h and 48 h in each of the mentioned 4 groups. Cellular cytotoxicity (quantitation of lactate dehydrogenase, LDH [11], in cell culture supernatant) was also evaluated in the same mentioned time periods (CytoTox 96® Non-Radioactive Cytotoxicity Assay G1782, Promega GloMax Multi Detection System).

Data from ovarian cortex tissue endothelial density (immunohistochemistry data) and LDH quantification in cell culture supernatant, were analysed using the proc glimmix of SAS (Statistical Analysis Systems, SAS Inst., Inc., Cary, N.C., USA). The models included treatments and hours as fixed effects, and animal (cow) as random (co-variable) effect. The means of each treatment/hours were calculated and compared by the PDIFF multiple comparison test. The differences were considered significant for $P \leq 0.05$.

Results

Endothelial Cell Density (Factor VIII Immunolocalization)

Treatment Effect

Both medical grade groups (L-Mesitran Soft and Ointment), presented higher density ($P<0.001$; $0.3905 \pm 0.1488$ and $0.3914 \pm 0.1486$ respectively) when compared to the VEGF and Control groups. Also, VEGF group presented higher values ($P=0.005$; $0.2942 \pm 0.1486$) than the Control group ($0.2256 \pm 0.1488$). No differences were observed between Soft and Ointment groups ($P=0.97$).

Time-Period Effect

Significant differences were observed between all hours ($P<0.001$), except for the combination between 4 h and 24 h ($P=0.5$). The 48 h time period presented the highest density value ($P<0.01$; $0.4992 \pm 0.1489$).

Treatment and Time-Period Effect (Interaction)

The 24 h time-period presented lower density values ($P<0.01$) than the 48 h period (highest value in each group), in the 3 treatment groups (VEGF, SOFT and OINTMENT). On the other hand, no significant differences were observed ($P=0.6$) at the 48 h time-period between both Soft and Ointment groups ($0.6932 \pm 0.1531$ and $0.6610 \pm 0.1526$ respectively).

From the observed results of the endothelial density, both Medical Grade Honey groups presented the highest values in relation to the VEGF and Control groups ($P<0.001$), with the highest value observed at the 48 h time-period ($P<0.001$).

Cytotoxicity (Lactate Dehydrogenase; LDH)

LDH is released during tissue damage, being a marker in direct proportion to cytotoxicity (higher LDH values indicate higher cytotoxicity). No statistically significant differences were detected between different groups/time periods. However, although both the Control and VEGF groups exhibit an increasing trend over the analysed time periods (4 h, 24 h and 48 h), the same is not true for the L-Mesitran groups, where there is a decreasing trend (lower cytotoxicity) between 24 h and 48 h, with a higher reduction rate for the Soft group (4.42% reduction; 1,046 fold) in relation to the Ointment group (2.36% reduction; 1.024 fold). This trend could be associated with the intrinsic production of hydrogen peroxide by honey, which is also a source of its antibacterial activity. It is produced by the action of glucose oxidase initially, followed by a decline in the 24 h-48 h period time period.

On basis of the above the results showed that the addition of medical grade honey during ovarian cortex culture induced superior endothelial density and an apparent tendency to reduce cellular toxicity. L-Mesitran (medical grade honey; Triticum) has already showed excellent cytocompatibility with other in vitro tissue cell cultures, also promoting a uniform increase in early cell proliferation and cell counts (also evident immediately adjacent to the product, suggesting no local toxicity) when compared with the untreated control groups. Moreover, pseudotubule stimulation was observed in an endothelial in vitro proliferation assay. Furthermore, it exhibits antimicrobial and antimycotic activity that can be important in in vitro cell cultures, and in the vitrification of bovine oocytes using a 1M honey (a major component of L-Mesitran) concentration, improved their post-warming maturation ability and embryonic development. VEGF for instance has been widely used in several studies, both in vivo and in vitro, involving the promotion of vascularization and viability, including the ovarian tissue. As an example, subcutaneously-transplanted mouse ovarian tissues previously soaked (in vitro) with a VEGF containing reagent, showed improved revascularization, survival, and oocyte quality. However, besides being expensive, vascular targeted therapy through VEGF (and other pro-angiogenic molecules) inhibition, currently represent a promising approach for patients with resistant (and recurrent) ovarian cancer which may prevent the use of this reagent for this proposal, in the near future. VEGF also exhibits a short half-life, and excessive amounts may cause vascular leakage.

The results obtained in this application in an animal (bovine) ovarian tissue model, may indicate this type of Medical Grade Honey (L-Mesitran) as an adjuvant in ovarian tissue preservation, compared to other more expensive and potentially more cytotoxic reagents.

The present inventors showed that the endothelial cell density after 48 hours was higher in the honey group than in the current (VEGF) group, demonstrating greater efficacy in fulfilling this purpose.

On basis of the above discussed experiments: Endothelial cell density (Factor VIII immunolocalization): From the observed results of the endothelial density, both Medical Grade Honey groups presented the highest values in relation to the VEGF and Control groups ($P<0.001$), with the highest value observed at the 48 h time-period ($P<0.001$). For Cytotoxicity (LDH): No statistically significant differences were detected between different groups/time periods. However, contrarily to the other groups, the L-Mesitran groups exhibited a decreasing trend (lower cytotoxicity) between 24 h and 48 h, [4.42% (Soft) and 2.36% (Ointment) reduction].

The present results show that the addition of Medical Grade Honey during ovarian cortex culture induced better endothelial density and an apparent tendency to reduce cellular toxicity.

The present inventors also noticed that current treatment methods with VEGF are very costly (several thousands of euros). Therefore the honey preparation can be significantly more affordable and thus more easily accessible. This may reflect not only in terms of increased research output but also on potential solutions to the fertility-related problems of populations with less acquisitive power. Additionally the antioxidants present in the honey based preparation may provide the added benefit of further reducing ischemic damage through the removal of free oxygen radicals responsible for cell membrane damage and lipid peroxidation.

What is claimed is:
1. A method of preserving human and/or animal ovarian follicles, comprising:
    contacting said human and/or animal ovarian follicles with a medical grade honey based ingredient, wherein said contacting promotes angiogenesis in said human and/or animal ovarian follicles.

2. The method of claim 1, wherein said composition comprises eco-honey (CAS 8028-66-8) in a concentration of 20-60% w/w.

3. The method of claim 2, wherein said composition further comprises hypo allergenic lanolin (CAS 8006-54-0) in a concentration of 5-20 w/w.

4. The method of claim 2, wherein said composition further comprises one or more components selected from the group consisting of PEG (CAS 57-55-6), PEG 4000 (CAS 25322-68-3), ascorbic acid (CAS 50-81-7), Vitamin A, Vitamin D, vitamin E, and Omega 3.

5. A method of preserving human and/or animal sperm cell viability, comprising:
    contacting said human and/or animal sperm cell with a medical grade honey based ingredient, wherein said contacting promotes angiogenesis in said human and/or animal sperm cell.

6. A method of preserving human and/or animal ovarian follicles and reducing cytotoxicity, comprising:
    contacting said human and/or animal ovarian follicles with a medical grade honey based composition comprising eco-honey (CAS 8028-66-8) in a concentration of 20-60% w/w, wherein said contacting promotes angiogenesis in said human and/or animal ovarian follicles.

* * * * *

UNITED STATES PATENT AND TRADEMARK OFFICE
CERTIFICATE OF CORRECTION

PATENT NO. : 11,160,272 B2  
APPLICATION NO. : 16/764575  
DATED : November 2, 2021  
INVENTOR(S) : Josephus Petrus Lidwinus Postmes Page 1 of 1

It is certified that error appears in the above-identified patent and that said Letters Patent is hereby corrected as shown below:

In the Claims

Claim 3, Column 7, Line 8 reads:
"in a concentration of 5-20 w/w."

Whereas it should read:
"in a concentration of 5-20% w/w."

Signed and Sealed this
Twenty-eighth Day of December, 2021

Drew Hirshfeld
*Performing the Functions and Duties of the*
*Under Secretary of Commerce for Intellectual Property and*
*Director of the United States Patent and Trademark Office*